(12) United States Patent
Brown et al.

(10) Patent No.: US 6,719,967 B1
(45) Date of Patent: Apr. 13, 2004

(54) HAIR TREATMENT COMPOSITIONS

(75) Inventors: Charles Rupert Telford Brown, Bedford (GB); Peter Fairley, Wirral (GB); Stanley Lam, Pleasent Hill, CA (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 854 days.

(21) Appl. No.: 09/282,708

(22) Filed: Mar. 31, 1999

(30) Foreign Application Priority Data

Apr. 3, 1998 (GB) ............................................. 9807271

(51) Int. Cl.[7] .............................. A61K 7/06; A61K 7/11; A61K 7/00; A61K 9/00
(52) U.S. Cl. ................ 424/70.1; 424/70.11; 424/70.12; 424/70.15; 424/400; 424/401; 514/944
(58) Field of Search ................... 424/400, 401, 424/70.1, 70.11, 70.12, 70.13; 514/944

(56) References Cited

U.S. PATENT DOCUMENTS

| | | | |
|---|---|---|---|
| 3,958,581 A | 5/1976 | Abegg et al. | |
| 3,962,418 A | 6/1976 | Birkofer | |
| 4,009,256 A | 2/1977 | Nowak, Jr. et al. | |
| 4,152,416 A | 5/1979 | Spitzer et al. | |
| 4,477,375 A | * 10/1984 | Grollier | 252/542 |
| 5,089,269 A | 2/1992 | Noda et al. | |
| 5,286,405 A | 2/1994 | Rennie et al. | |
| 5,534,265 A | * 7/1996 | Fowler et al. | 424/489 |
| 5,609,857 A | * 3/1997 | Chandran et al. | 424/70.1 |
| 5,635,171 A | 6/1997 | Nadaud | |
| 5,641,480 A | * 6/1997 | Vermeer | 424/70.24 |
| 5,700,455 A | * 12/1997 | Hinterwaldner et al. | 424/70.14 |

FOREIGN PATENT DOCUMENTS

| | | |
|---|---|---|
| DE | 297 15 709 | 2/1999 |
| EP | 0355908 | 2/1990 |
| EP | 0498119 | 8/1992 |
| EP | 0567326 | 10/1993 |
| EP | 0590538 | 4/1994 |
| WO | 92/10989 | 7/1992 |
| WO | 95/12988 | 5/1995 |
| WO | 95/22311 | 8/1995 |
| WO | 96/31188 | 10/1996 |
| WO | 97/23194 | 7/1997 |
| WO | 98/08601 | 3/1998 |

OTHER PUBLICATIONS

Lewis, Sr. R.J., "Hawley's Condensed Chemical Dictionary", p. 1066, 1997.

* cited by examiner

*Primary Examiner*—Thurman K. Page
*Assistant Examiner*—Marina Lamm
(74) *Attorney, Agent, or Firm*—Milton L. Honig (57) ABSTRACT

A hair treatment composition which has a thickened fluid form comprising:

(i) a first (shear gel) phase comprising at least one naturally derived polymer which is capable of forming a reversible gel, which polymer is present in the composition as a shear gel (i.e., a multiplicity of separate gel particles which have been formed by subjecting the polymer to shear while gel formation takes place), and (ii) a second (suspended) phase suspended therein.

2 Claims, 1 Drawing Sheet

HAIR TREATMENT COMPOSITIONS

FIELD OF THE INVENTION

This invention relates to hair treatment compositions. In particular the invention relates to hair treatment compositions comprising a phase formed from a particular type of gel.

BACKGROUND AND PRIOR ART

A suspending agent is commonly employed in hair treatment compositions to improve stability against phase separation and settling of suspended materials.

Examples of commonly used suspending agents include crystalline suspending agents (such as ethylene glycol distearate) and inorganic structurants (such as swelling clays). Although these materials are effective for suspending particulate matter, they can adversely affect lathering performance and impart an undesirable cloudy appearance to the composition. Furthermore, during use of the composition they tend to get co-deposited along with the ingredients it is desired to deposit, which can lead to dulling of the hair through excessive build up and reduced performance.

The prior art also proposes the use for suspending purposes of hydrophilic polymers which disperse in aqueous media. Natural polymers have been used for this purpose, and in particular xanthan gum has been used. Personal washing products, especially shampoos, containing xanthan gum are described for example in U.S. Pat. No. 5,286,405 and GB-A-2188060.

A problem is that the resulting products often have an unacceptable "stringy" texture and a slimy feel.

One category of synthetic polymers used for suspending purposes are carboxyvinyl polymers. The carboxyvinyl polymers are colloidally water soluble polymers of acrylic acid cross-linked with polyallylsucrose or polyallylpentaerythritol, obtainable under the CARBOPOL trademark from B F Goodrich. U.S. Pat. No. 5,635,171 describes a transparent or translucid gel based on such polymers, in which the gel is rigidified by the incorporation of a very small quantity of an aqueous solution of galactomannan (carob, guar or tara gum). This rigidification enables the stabilization of suspended phases.

A problem is, however, that carboxyvinyl polymers of the above described type can be difficult to formulate because of, inter alia, their sensitivity to pH and ionic strength and their incompatibility with ethoxylated surfactants.

A number of polymers of biological origin, when in aqueous solution, have the ability to form so-called reversible gels which melt when heated but revert to a gel when cooled down subsequently. One well known example of a polysaccharide which forms reversible gels is agar. An aqueous solution containing a small percentage of agar is a mobile liquid when hot, but when left to cool it forms a gel with sufficient rigidity to maintain its own shape. Other naturally derived polymers which can form reversible gels are carrageenan, furcelleran, gellan and pectin.

The formation of gels by natural polysaccharides arises from interaction between the polymer molecules. Reversible gels generally display a melting temperature or temperature range, referred to as the gel point. This is the temperature at which, on slow heating, the gel is observed to melt as this interaction largely disappears. Thus, above the gel point, the hot solution of polymer is mobile. When it cools below its gel point, the interaction of polymer molecules enables them to form a continuous and branched network which extends throughout the sample. In contrast with the formation of a continuous, branched network, some other materials which thicken water do so through merely local, transient entanglement of molecules. A discussion of polysaccharide gels, including their range of mechanical properties, is found in "Gels and Gelling" by Allan H Clark which is Chapter 5 in Physical Chemistry of Foods, Schwartzberg and Hartel, editors; published by Marcel Dekker 1992. In some instances there is hysteresis and the melting and setting temperatures are not identical.

The melting temperature of a gel can suitably be measured by placing a steel ball, having a diameter of approximately 1 mm, on the surface of a sample which is fully set, then raising the temperature slowly, e.g., in a programmable water bath. The gel melting point is the temperature at which the ball begins to sink through the sample. Apparatus to facilitate such determinations is available, for example as a Physica AMV200 rolling ball viscometer from Anton Paar KG.

A reversible gel also displays a transition temperature at which, upon slow temperature increase, all ordering, be it of microscopical or macroscopical extent, has disappeared completely. This transition temperature (from order to disorder) can be measured by means of differential scanning calorimetry (DSC). The transitions temperature of a reversible gel, as measured by DSC, usually approximately coincides with gel melting, observable visually.

EP-A-355908 teaches that polysaccharides which are capable of forming a reversible gel can be used to form viscous, yet mobile, fluid compositions by subjecting the composition to shear while gel formation takes place. The resulting compositions can be termed "shear gels".

We have now found that hair treatment compositions comprising a continuous phase formed from such shear gels display excellent resistance to phase separation and settling of suspended materials. The shear gels are tolerant to the presence of surfactant, and may under some circumstances boost the conditioning performance of the hair treatment composition.

WO98/08601 describes aqueous compositions such as liquid personal cleansers containing large hydrogel particles formed by two different water soluble polymers. The hydrogel particles trap water insoluble benefit agents in a network formed by these two polymers. The system is not a shear gel since it is prepared by first forming elongated polymer gel noodles which after gel formation are subsequently cut/broken into the desired gel particle size. The second polymer (which is typically an acrylic polymer such as CARBOPOL referred to above) is required to modify gel strength in order to help stabilize benefit agent in the polymer hydrogel system.

WO95/12988 refers to suspensions or dispersions of gelled and hydrated biopolymer particles for use in food or personal care products to impart a fatty-like character to the product. This system is not a shear gel since particulation of dry material at a temperature equal to or above T(gel) is followed by hydration of the particles at a temperature lower than T(gel), the term "T(gel)" denoting the temperature at which, upon cooling, an aqueous solution of the biopolymer concerned, sets to a gel.

SUMMARY OF THE INVENTION

In a first aspect, the present invention provides a hair treatment composition which has a thickened fluid form comprising:

(i) a first (shear gel) phase comprising at least one naturally derived polymer which is capable of forming a reversible gel, which polymer is present in the composition as a shear gel (i.e., a multiplicity of separate gel particles which have been formed by subjecting the polymer to shear while gel formation takes place), and (ii) a second (suspended) phase suspended therein.

In a second aspect, the invention provides the use of a shear gel as a suspending system in a hair treatment composition.

DETAILED DESCRIPTION AND PREFERRED EMBODIMENTS

FIRST (SHEAR GEL) PHASE

In the present specification, the expression "thickened fluid" is used to denote a composition with viscosity greater than that of water.

In order that the gel particles remain stable in the presence of surfactant (which will normally be present in hair treatment compositions of the invention), it will generally be desirable that the polymer does not require polyvalent cations in order to form the precursor aggregates that are subsequently capable of intermolecular association leading to formation of a gel network. Consequently, it is desirable that the polymer is capable of forming a reversible gel when dissolved at a sufficient concentration in hot distilled or demineralised water and allowed to cool to an ambient temperature of 20° C.

Compositions embodying this invention may be made with viscosities in a wide range. At one extreme, the compositions may be freely mobile, self-levelling and pourable, although thicker than water. On the other hand, they may be made as viscous liquids which can be squeezed from a collapsible container, and yet which are too viscous to pour, except very slowly.

They are shear-thinning, which can be a useful property in hair treatment compositions such as shampoos and conditioners, because the user can perceive the product as thick and viscous, and yet find it easy to apply. An advantage of viscous shear gels is that they are good at retaining the shape which has been squeezed out, and so can be dispensed by methods other than simple pouring such as from flexible or deformable squeeze tubes.

If the compositions are heated to a temperature above the melting and transition temperatures, the individual gel particles will melt and will not reform as separate particles on cooling, but this will not be a problem in ordinary use, because reversible gels generally have melting temperatures well above normal room temperatures.

Viscosity of compositions embodying this invention can be measured using the same techniques as are used to measure viscosities of other thickened liquid compositions. One suitable apparatus is the Haake Rotoviscometer, another is the Carri-Med CSL 500 viscometer.

Many compositions of this invention will display a viscosity in a range from 0.1 Pa.s to 1000 Pa.s at a shear rate of 10 $sec^{-1}$ measured at 20° C.

One route for the preparation of the sheared gel particles required for this invention starts with the provision of an aqueous solution of the polymer, at a temperature above the gel melting temperature (and probably also above its order to disorder transition temperature), then cooling the solution to a temperature below the gel setting temperature, while applying shear to the composition. Generally, the solution will be subjected to shear while cooling from 60° C. or above to 25° C. or less.

On a small scale, this may be carried out in a beaker with a mechanical stirrer in the beaker, providing vigorous stirring while the contents of the beaker are allowed to cool.

We prefer to carry out the preparation using a scraped surface heat exchanger. This may be equipped to operate under a partial vacuum to reduce the incorporation of air bubbles into the composition as gel formation takes place.

Another possibility for preparing the gel particles is to form a bulk quantity of the gel and then break this up into small particles, for instance by pumping it through a homogeniser.

We have found that for many polymers gel formation is inhibited by the presence of surfactant (which is normally a component of hair treatment compositions), and yet gel particles which have already been formed remain stable if surfactant is added subsequently.

Therefore, generally it will be desirable to form the gel particles by cooling an aqueous solution of the gel-forming polymer in the substantial absence of surfactant, and then add surfactant subsequently. An alternative approach is to incorporate surfactant into the aqueous composition before the step of cooling under shear, but this is not possible for all gel-forming polymers.

Thus, in a further aspect, this invention provides a method of preparing a hair treatment composition as set forth above which comprises forming a hot, mobile aqueous solution of the polymer, cooling the solution through its gel temperature, subjecting it to shear during or after cooling, and incorporating surfactant possibly before but preferably after cooling through the gel temperature.

A laboratory-scale scraped surface heat exchanger which we have used successfully is the ESCO Labor mixer available from ESCO Labor, CH-4125, Reihen, Germany.

Scraped surface heat exchangers and homogenisers are used in the commercial production of margarine and other spreadable foodstuffs and such apparatus may be used to produce compositions of this invention on a larger scale. A discussion of such heat exchangers is given by Harrod in Journal of Food Process Engineering 9 (1986) pages 1–62. Suppliers of such apparatus include Armfield Ltd, Ringwood, Hampshire, England, Contherm Corporation which is a division of the Alfa-Laval Group, USA and APV Projects (Crepaco) Ltd, Crawley, West Sussex, England.

After the formation of gel particles, the addition of surfactant or other ingredients, probably as a liquid concentrate, can be carried out using conventional mixing apparatus, operating at low shear. Possibly a scraped surface heat exchanger used to form the gel particles can also be used for a subsequent mixing operation, especially if run more slowly, so as to give lower shear. A mixing operation should not be allowed to heat the composition sufficiently to cause the melting of the gel particles. If necessary, a composition containing gel particles should be cooled before and/or during any subsequent mixing operation.

Materials and procedures useful in this invention will now be described in greater detail, making reference to the accompanying drawings wherein.

Figure 1:
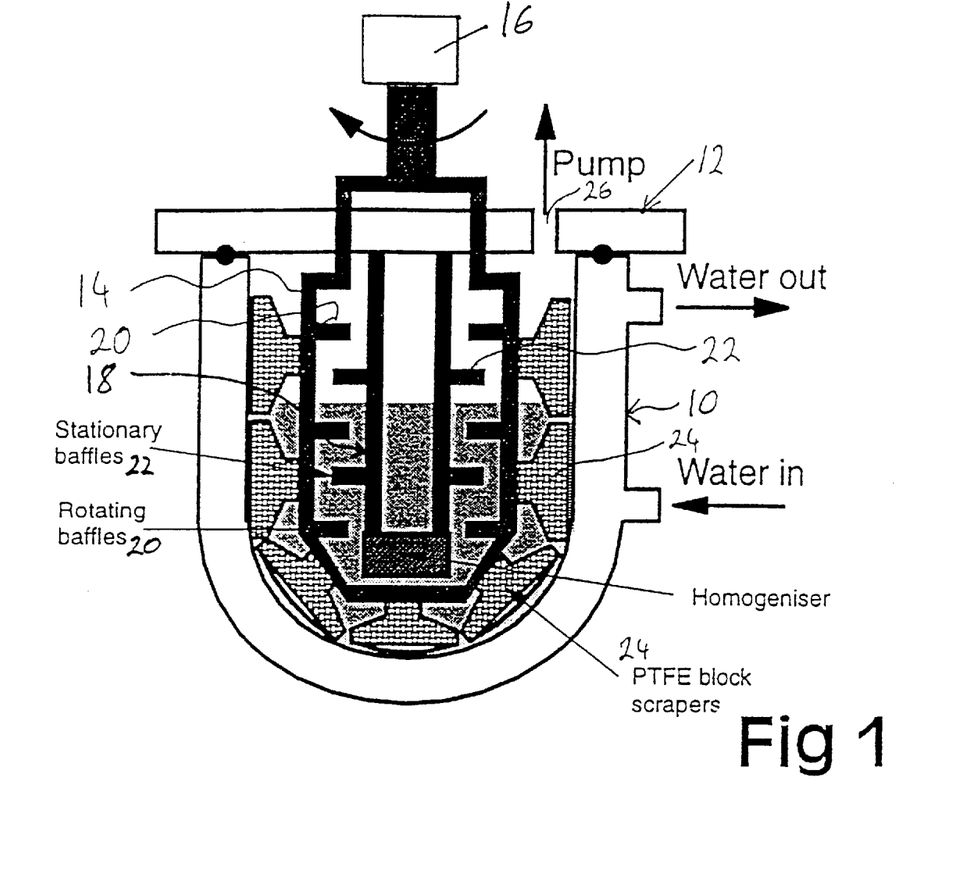
FIG. 1 is a cross-section of a mixer useful for preparing shear gel particles on a batch basis, and FIG. 2 diagrammatically illustrates apparatus for continuous preparation.

The apparatus shown in FIG. 1 is a TK Agi homo mixer. It has a containing vessel 10 with inner and outer walls spaced apart to allow a coolant to be circulated through the space between them. The vessel has an upper closure 12. A rotor 14 within the vessel is extended through the upper closure 12 and connected to a drive motor 16. The rotor 14 surrounds a central fixed stator 18. Baffles 20, 22 project from the rotor and stator respectively. When the rotor is turned, the liquid within the vessel 10 is subjected to shear by the movement of the rotor 14 and its baffles 20 relative to the stator 18 and its baffles 22. In addition flaps 24 made of polytetrafluoroethylene projecting from the rotor 14 scrape the inner wall of the vessel 10. The upper closure 12 includes provision at 26 for connection to a vacuum pump. Gas tight seals are provided between the rotor 14 and the upper closure 12. Consequently vacuum can be applied to the interior of the vessel 10 through the connection 26.

In order to make a composition according the invention using this apparatus an aqueous solution of the polymer, heated to above its gel temperature, is placed in the vessel. The upper closure 12 is then placed on the vessel and the contents of the vessel are cooled by circulation of coolant through the space between the vessel walls. At the same time the rotor is turned and vacuum is applied to the connection 26 so that cooling of the vessel contents takes place under conditions of shear, while suction through the air outlet 26 prevents formation of gas bubbles.

In consequence, as the contents of the vessel cool to below the gel point, a multiplicity of small gel particles are formed. Once the contents of the vessel have cooled below the gel temperature and these particles have formed, surfactant can be mixed with the vessel contents either by removing the upper closure and adding a liquid concentrate of the surfactant to the vessel 10, or by transferring the contents of the vessel 10 and also the surfactant, to a separate mixer.

Figure 2:
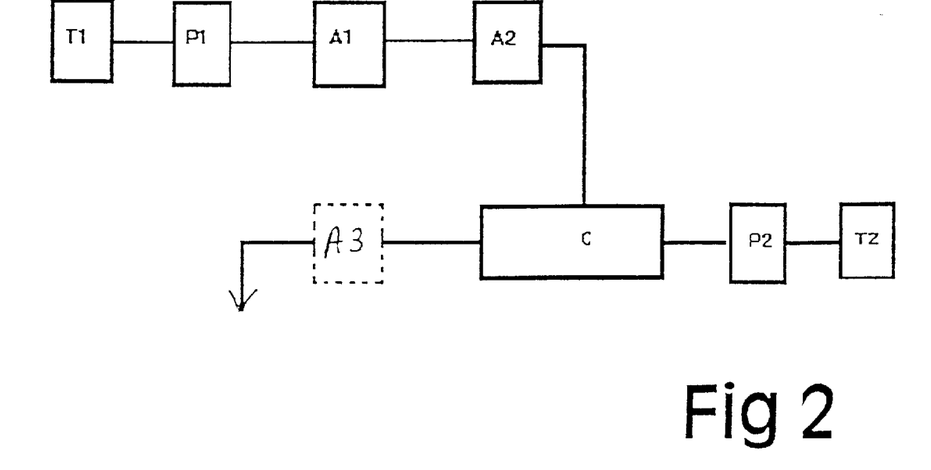

FIG. 2 illustrates a preferred form of apparatus consisting of several individual pieces of equipment connected together by pipework.

A hot aqueous solution of the polymer is prepared and held in a supply vessel T1. It is delivered from this by a suitable pump P1 to a scraped surface heat exchanger A1 which is in the form of a cylinder for through flow of the polymer solution and which is surrounded by a jacket for coolant. Within this heat exchanger is located a large diameter shaft fitted with scraper blades which are spring loaded to hold them against the interior surface of the cylindrical vessel wall. Rotation of this central shaft by a motor applies shear to the polymer solution as it passes through the heat exchanger A1.

As the polymer solution passes through the heat exchanger A1 it is cooled to below its gel temperature under conditions of shear and this leads to the formation of gel particles in a continuous aqueous phase. The resulting compositions passes on from heat exchanger A1 to a second heat exchanger A2 which is similar except that it operates at a lower speed. This is used to cool the composition further.

The composition then flows on to a mixer C which, like the units A1 and A2 performs a heat exchange function. However, within this C-unit there are stationary baffles projecting inwardly from the heat exchanger walls and a motor driven central, small diameter shaft which carries further baffles that project between the stationary baffles of the cylinder wall. There are no scrapers in this device. Here the composition is mixed with surfactant solution delivered from a supply vessel T2 by means of a suitable pump P2. The mixture leaving the high speed mixer C is a composition in accordance with the present invention. It may be convenient to cool it by passage through a further scraped surface heat exchanger A3 operating at low speed before the composition is delivered as finished product or packed in containers. The pumps P1 and P2 may conveniently be provided as separate channels of a proportioning piston pump, which is a convenient way to ensure that constant proportions are delivered from each of the tanks T1, T2.

Mixing apparatus, pumps and scraped surface heat exchangers used in apparatus as above can be of types which are customarily used in the production of margarine and other edible spreads. Another name for the scraped surface heat exchanger which provides for through flow of the material is a "votator". These pieces of apparatus may be manufactured in a range of sizes extending from small units which can fit on a laboratory bench to full scale production plant. Manufacturers of such apparatus include Armfield Ltd., Contherm Corporation and APV Projects (Crepaco) Ltd mentioned above.

Polymer Types

Compositions of this invention contain a naturally derived polymer capable of forming a reversible gel. It is desirable that the polymer should be capable of forming a gel without requiring metal salt to be present. (Polymers which require ionic species to be present as a prerequisite for gel formation are apt to be destabilised by surfactant, even if formed as shear gel particles). Generally, this means that such a polymer, dissolved in demineralised water at some concentration between 0.1 and 10% by weight will form a gel on cooling the solution without agitation from an elevated temperature of 90° C. to 20° C. for 24 hours.

In this test of gel-formation, a polymer may or may not form a gel at every concentration in the range from 1 to 10% by weight. With some polymers, concentrations as high as 10% by weight may not be achievable. Some polymers may form gels without standing for as long as 24 hours.

The naturally derived polymer which is capable of forming a reversible gel will usually be one or more polysaccharides.

One polysaccharide which may be used is agar, which is of course well known for use as a growth medium for microorganisms in vitro.

Agarose is a linear polysaccharide, basically made up from β-1,3 galactose residues alternating with α-1,4 galactose residues. The latter are present as the 3,6 anhydride and are the L-enantiomer.

Agaropectin likewise has β-1,3 galactose residues alternating with α-1,4 galactose residues, but includes sulphate, pyruvate and/or glucuronic acid residues.

The term agar covers a family of polymers containing agarose and/or agaropectin, i.e., polymers with backbone structure containing alternating 1,3-D-galactose and 1,4-L-galactose residues.

Agar is extracted from certain species of red seaweed, principally in Japan. A description of agar is given by Tetsujiro Matsuhashi as Chapter 1 in "Food Gels" edited by Peter Harris, Elsevier, 1990.

Another category of polysaccharide which may be used is the kappa carrageenan. Carrageenans are a class of polysaccharides which occur in some other red seaweed species. They are linear polysaccharides made up from alternating β-1,3- and α-1,4-linked galactose residues. The 1,4-linked residues are the D-enantiomer and sometimes occur as the 3,6-anhydride. Many of the galactose residues are sulphated.

A number of carrageenan structures have been described and commercial materials are available which approximate to the ideal structures. However, variations between these structures occur, depending on the source of the carrageenan and treatment of it after extraction.

A description of different carrageenan types is given in "Carrageenans" by Norman F Stanley which is Chapter 3 of "Food Gels" mentioned above.

Kappa carrageenan is sulphated on the 1,3-linked galactose residues, but not on the 1,4-linked residues. Iota carrageenan is sulphated on both residues. Lambda carrageenan has two sulphate groups on the 1,4-linked residues and one sulphate group on 70% of the 1,3-linked residues.

Other types of carrageenan may be used in mixtures with kappa. Aqueous solutions of iota carrageenan exist as reversible gels, but these appear to be self-healing. Iota carrageenan can be used to form compositions in accordance with this invention, but the compositions become lumpy during storage because of the self-healing property of iota carrageenan gels, and so for this invention it is desirable to use kappa carrageenan or mixtures of kappa and iota.

Lambda carrageenan on its own in aqueous solution does not form gels because its higher charge density inhibits association between molecules and consequent structuring in liquids. However, some lambda carrageenan may be included in mixtures with kappa, or may be present as an impurity in commercial supplies of kappa or iota carrageenan.

If lambda carrageenan is included in a mixture of carrageenans, the mixture may contain a majority (more than one half of the polysaccharide) of kappa or kappa and iota carrageenan with a minority proportion of lambda carrageenan.

Another polymer which may be used is furcellaran. Furcellaran is similar to kappa carrageenan, but is only partially sulphated on the 1,3-linked galactose residues. A polymer of bacterial origin which may be used is gellan. It is the polymer of a tetrasaccharide repeat unit, containing glucose, glucuronic acid, and rhamnose residues. There is some substitution with acyl groups but these are often removed during production to give a low acyl gellan. Gellans are the subject of Chapter 6 by G R Saunderson in "Food Gels" mentioned above. Another possibility is to use a so-called synergistic gel which relies on the interaction of two polymer types. In general these may be formed from a polysaccharide which is a glucomannan with sequences of mannose residues in its polymer chain, such as locust bean gum or guar gum, and a second polymer which is xanthan or carrageenan.

It is possible to include an additional thickening agent, such as a small concentration of xanthan gum, or curdlan, in the composition in addition to the gel particles. This may possibly be added after gel particles have been formed along with surfactant.

Polymer capable of forming a reversible gel may constitute from 0.1 to 10 wt. % of the whole composition, often from 0.1 to 5 wt. %.

In general, the viscosity of a shear gel composition in accordance with this invention will increase with the concentration of polymer contained in it.

Viscosity will also be affected by the size and shape of the gel particles, which in turn is affected by the conditions used to apply shear during cooling. In general, combinations of variable cooling rates and different rotor speeds during shearing permits the optimisation of particle dispersion smoothness, suspending properties and viscosity, possibly because gel particle shapes can vary between spherical and filamentous forms.

Non-surfactant Electrolyte

Although it is generally desirable that the polymer should be capable of forming a gel without participation of ionic species, some polymers which are capable of forming a gel in distilled or demineralised water, nevertheless, forms gels of greater viscosity if some electrolyte is present. Notably the viscosity of Kappa carrageenan gel dispersions is increased by the presence of potassium ions and the viscosity of agar gel dispersions is increased in the presence of calcium ions. Consequently, a polymer solution which is cooled under shear to form gel particles as required for this invention may include electrolyte to enhance the strength of the resulting gel particles. The amount of electrolyte required may be a small percentage of the product, e.g. 1%.

Second (Suspended) Phase

The suspended phase in the hair treatment composition may comprise any material which it is usually desired to incorporate in hair treatment compositions and which requires some degree of stabilization in the hair treatment composition against phase separation and settling under normal storage conditions.

The suspended phase may suitably be selected from one or more of the following classes of material:

Conditioning Agents

As used herein, the term "conditioning agent" includes any material which is used to give a particular conditioning benefit to hair and/or skin. For example, in compositions for use in washing hair, such as shampoos and conditioners, suitable materials are those which deliver one or more benefits relating to shine, softness, combability, wet-handling, anti-static properties, protection against damage, body, volume, stylability and manageability.

Preferred conditioning agents for use in the present invention include emulsified silicones, used to impart for example wet and dry conditioning benefits to hair such as softness, smooth feel and ease of combability.

Various methods of making emulsions of particles of silicones for use in the invention are available and are well known and documented in the art.

The viscosity of the silicone itself (not the emulsion or the final washing composition) preferably ranges from 10,000 cps to 5 million cps. The viscosity can be measured by means of a glass capillary viscometer as set out further in Dow Corning Corporate Test Method CTM004 Jul. 20, 1970.

Suitable silicones include polydiorganosiloxanes, in particular polydimethylsiloxanes which have the CTFA designation dimethicone. An example is dimethicone fluid having a viscosity of up to 100,000 centistokes at 250° C., which is available commercially from the General Electric Company as the Viscasil series and from Dow Corning as the DC 200 series.

Aminofunctional silicones which have the CTFA designation amodimethicone, are also suitable for use in the compositions of the invention, as are polydimethyl siloxanes having hydroxyl end groups, which have the CTFA designation dimethiconol.

Also suitable are silicone gums. "Silicone gum" denotes polydiorganosiloxanes having a molecular weight of from 200,000 to 1,000,000 and specific examples include dimethicone gums, dimethiconol gums, polydimethyl siloxane/diphenyl/methylvinylsiloxane copolymers, polydimethylsiloxane/methylvinylsiloxane copolymers and mixtures thereof. Examples include those materials described in U.S. Pat. No. 4,152,416 (Spitzer), and on General Electric Silicone Rubber product Data Sheet SE 30, SE 33, SE 54 and SE 76.

Also suitable for use in the present invention are silicone gums having a slight degree of cross-linking, as are described for example in WO 96/31188. These materials can impart body, volume and stylability to hair, as well as good wet and dry conditioning.

Preferred emulsified silicones for use in compositions of the invention have an average silicone particle size in the composition of less than 100, preferably less than 30, more preferably less than 20 microns, most preferably less than 10 microns.

Particle size may be measured by means of a laser light scattering technique, using a 2600D Particle Sizer from Malvern Instruments.

Suitable silicone emulsions for use in the invention are commercially available in a pre-emulsified form. This is particularly preferred since the pre-formed emulsion can be incorporated into the washing composition by simple mixing.

Examples of suitable pre-formed emulsions include emulsions DC2-1766 and DC2-1784, available from Dow Corning. These are emulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum.

The amount of silicone incorporated into the compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by weight of the total composition, is a particularly suitable level.

A further preferred class of conditioning agents are peralk(en)yl hydrocarbon materials, used to enhance the body, volume and stylability of hair.

EP 567 326 and EP 498 119 describe suitable peralk(en)yl hydrocarbon materials for imparting stylability and enhanced body to hair. Preferred materials are polyisobutylene materials available from Presperse, Inc. under the PERMETHYL trade name.

The amount of per-alk(en)yl hydrocarbon material incorporated into the compositions of the invention depends on the level of body and volume enhancement desired and the specific material used. A preferred amount is from 0.01 to about 10% by weight of the total composition although these limits are not absolute. The lower limit is determined by the minimum level to achieve the body and volume enhancing effect and the upper limit by the maximum level to avoid making the hair unacceptably stiff. We have found that an amount of per-alk(en)yl hydrocarbon material of from 0.5 to 2% by weight of the total composition is a particularly suitable level.

Solid Active Agents

Examples of typical solid active agents include antimicrobials such as the heavy metal salts of pyridinethione, especially zinc pyridinethione, other antimicrobials such as climbazole, piroctone olamine, selenium sulphide and ketoconazole. These substances typically have an average particle diameter of from about 0.2 to about 50 microns, preferably from about 0.4 to about 10 microns.

Where the solid active agent is an antimicrobial agent, such as zinc pyridinethione, this may be suitably be employed in the composition in an amount of from 0.001% to about 1% by weight of the total composition.

Other suitable solid active agents include pigment particles, such as solid dyes or colorants suitable for application to hair, and metal colloids.

Aesthetic Agents

Hair treatment compositions such as shampoos and conditioners are frequently opacified or pearlised to enhance consumer appeal.

Examples of opacifying agents include higher fatty alcohols (e.g. cetyl, stearyl, arachidyl and behenyl), solid esters (e.g. cetyl palmitate, glyceryl laurate, stearamide MEA-stearate), high molecular weight fatty amides and alkanolamides and various fatty acid derivatives such as propylene glycol and polyethylene glycol esters. Inorganic materials used to opacify hair treatment compositions include magnesium aluminium silicate, zinc oxide, and titanium dioxide.

Pearlescing agents typically form thin, platelet-type crystals in the composition, which act like tiny mirrors. This gives the pearl lustre effect. Some of the opacifying agents listed above may also crystallise as pearlescing agents, depending on the media in which they are used and the conditions employed.

Typical pearlescing agents may be selected from C16–C22 fatty acids (e.g. stearic acid, myristic acid, oleic acid and behenic acid), esters of C16–C22 fatty acid with alcohols and esters of C16–C22 fatty acid incorporating such elements as alkylene glycol units. Suitable alkylene glycol units may include ethylene glycol and propylene glycol. However, higher alkylene chain length glycols may be employed. Suitable higher alkylene chain length glycols include polyethylene glycol and polypropylene glycol.

Examples are polyethylene glycol mono or diesters of C16–C22 fatty acids having from 1 to 7 ethylene oxide units, and ethylene glycol esters of C16–C22 fatty acids. Preferred esters include polyethylene glycol distearates and ethylene glycol distearates. Examples of a polyethylene glycol distearate available commercially are EUPERLAN PK900 (ex Henkel) or GENAPOL TS (ex Hoechst). An example of an ethylene glycol distearate is EUPERLAN PK3000 (ex Henkel).

Other pearlescing agents include alkanolamides of fatty acids having from 16 to 22 carbon atoms, (e.g. stearic monoethanolamide, stearic diethanolamide, stearic monoisopropanolamide and stearic monoethanolamide stearate); long chain esters of long chain fatty acids (e.g. stearyl stearate, cetyl palmitate); glyceryl esters (e.g. glyceryl distearate),long chain esters of long chain alkanolamides (e.g. stearamide DEA distearate, stearamide MEA stearate), and alkyl (C18–C22) dimethyl amine oxides (e.g. stearyl dimethyl amine oxide).

Further suitable pearlescing agents include inorganic materials such as nacreous pigments based on the natural mineral mica. An example is titanium dioxide coated mica. Particles of this material may vary in size from 2 to 150 microns in diameter. In general, smaller particles give rise to a pearly appearance, whereas particles having a larger average diameter will result in a glittery composition.

Suitable titanium dioxide coated mica particles are those sold under the trade names TIMIRON (merck) or FLAMENCO (Mearl).

The level of opacifying or pearlescing agent employed in compositions of the invention is generally from 0.01 to 20%, preferably 0.01 to 5%, more preferably from 0.02 to 2% by weight of the total composition.

Gas (e.g. air) bubbles represent another type of suspended phase that may be introduced into a hair treatment composition for aesthetic purposes. When evenly sized and homogeneously dispersed in the composition, these can enhance consumer appeal—a typical application is in a transparent or translucent composition such as a hair styling gel.

Product Form

Compositions of the present invention may be formulated as transparent or opaque emulsions, lotions, creams, pastes, or gels. Particularly preferred product forms are shampoos, conditioners and hair styling gels.

Shampoo Compositions

A particularly preferred hair treatment composition in accordance with the invention is a shampoo composition.

Such a shampoo composition will comprise one or more cleansing surfactants which are cosmetically acceptable and suitable for topical application to the hair. Further surfactants may be present as an additional ingredient if sufficient for cleansing purposes is not provided as emulsifier for any emulsified components in the composition, e.g. emulsified silicones. It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight of the total composition.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO-(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifier) in shampoo compositions of the invention is generally from 0.1 to 50% by weight, preferably from 5 to 30%, more preferably from 10% to 25% by weight of the total shampoo composition.

A cationic deposition polymer is a preferred ingredient in shampoo compositions of the invention, for enhancing conditioning performance of the shampoo. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

- copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
- copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);
- cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;
- mineral acid salts of amino-alkyl esters of homo-and co-polymers of unsaturated carboxylic acids having from 3 to 5 carbon atoms, (as described in U.S. Pat. No. 4,009,256);
- cationic polyacrylamides(as described in WO95/22311).

Other cationic deposition polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhodia (formerly Rhone-Poulenc) in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR C15, JAGUAR C17 and JAGUAR C16 and JAGUAR C162.

The cationic deposition polymer will generally be present at levels of from 0.001 to 5%, preferably from about 0.01 to 1%, more preferably from about 0.02% to about 0.5% by weight of the total composition.

Conditioners

Compositions in accordance with the invention may also be formulated as conditioners for the treatment of hair (typically after shampooing) and subsequent rinsing.

Such a conditioner will comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, e.g chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

In conditioners of the invention, the level of cationic surfactant is preferably from 0.01 to 10%, more preferably 0.05 to 5%, most preferably 0.1 to 2% by weight of the composition.

Conditioners of the invention advantageously incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Hair Styling Gels

Hair treatment compositions in accordance with the invention may also take the form of hair styling gels.

Such a hair styling gel will comprise a water soluble film-forming resin. The resin may either be anionic, nonionic, amphoteric or cationic. Specific resins include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether/maleic acid), and octylacrylamide/acrylate/butylaminoethyl methacrylate copolymers. Mixtures of resins may also be used. PVP and PVP copolymers with other monomers are preferred, e.g. copolymers of polyvinyl pyrrolidone and vinyl acetate, particularly in a 70/30 ratio.

Amounts of the film-forming resin may range from 0.1 to 20%, preferably from 1 to 10%, optimally from 2 to 5% by weight.

Small quantities of surfactant ranging anywhere from 0.1 to about 10%, preferably from about 0.1 to about 1%, most preferably about 0.3% by weight may be present in hair styling gels of the invention. The surfactant may be an anionic, nonionic or cationic emulsifier. Particularly preferred are nonionic emulsifiers which are formed from alkoxylation of hydrophobes such as fatty alcohols, fatty acids and phenols.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Examples:

EXAMPLES

Example 1—Shampoo Composition

A shampoo composition was prepared having a composition as set out in the following Table:

| Ingredient | Chemical Name | Supplier | active % |
|---|---|---|---|
| Empicol ESB 70 | ethoxylated sodium lauryl ether sulphate | Albright & Wilson | 14 |
| Amonyl 380 BAU | cocoamidopropyl betaine | Seppic | 2 |
| Timiron MP1001 | micaceous titanium dioxide | Merck | 0.2 |
| Perfume | | IFF | 0.55 |
| Jaguar C13S | guar hydroxypropyl trimonium chloride | Rhodia | 0.03 |
| Silicone DC2 1391 | polydimethylsiloxane microemulsion | Dow Corning | 0.8 |
| | vitamin E acetate | Roche, BASF | 0.05 |
| | sodium benzoate | Fisons | 0.5 |
| | phenoxyethanol | Seppic | 0.4 |
| | sodium chloride | BDH | 1 |
| | citric acid | BDH | ~0.33 |
| | sodium hydroxide | BDH | ~0.02 |
| Luxara 1253 | agar | Branwell | 0.15 |
| | Water | | to 100 |

The method of manufacture of the above shampoo composition is as follows:

Dissolve the agar in water at 95 deg C. to give a dilute agar solution. Cool the solution to 25 degrees with continuous stirring to form a shear gel. To this gel add the ethoxylated sodium lauryl ether sulphate, cocoamidopropyl betaine, micaceous titanium dioxide, polydimethylsiloxane microemulsion, perfume, guar hydroxypropyl trimonium chloride, sodium benzoate, phenoxyethanol, vitamin E acetate and most of the sodium chloride with vigorous stirring to ensure good dispersion. When the mixture is completely mixed (which may take some time) measure the viscosity using a Brookfield viscometer fitted with a number 4 spindle rotating at 20 rpm. Add more sodium chloride if necessary to bring the viscosity into the range of 4500–6000 centipoise. Measure the pH and add citric acid and/or sodium hydroxide as necessary to bring the pH into the range 4.5–5.0.

Example 2—Hair Conditioner

A hair conditioner was prepared having a composition as set out in the following Table:

| Ingredient | Chemical Name | Supplier | active % |
|---|---|---|---|
| Arquad 16–29 | cetyl trimethyl ammonium chloride | Akzo | 0.7 |
| Laurex CS | cetearyl alcohol | Albright & Wilson | 2.3 |
| Silicone DC2 1784 | polydimethylsiloxane emulsion | Dow Corning | 1.5 |
| Perfume | | IFF | 0.500 |
| | citric acid | BDH | ~0.03 |
| Para M | methyl paraben | Maprecos, Akzo | 0.2 |
| | D-glucose | Roquette | 0.1 |
| | L-isoleucine | Ajinomoto | 0.1 |
| Luxara 1253 | Agar | Branwell | 1.0 |
| | water | | to 100 |

The conditioner may be manufactured by 2 alternative methods as follows:

Method 1:

Dissolve the agar in water at 95 deg C. to give a dilute agar solution. Add cetrimonium chloride and cetearyl alcohol and stir well to ensure that they melt and mix. Cool the solution to 25 degrees with continuous stirring to form a shear gel. To this gel add the polydimethylsiloxane emulsion, perfume, methyl paraben, D-glucose and L-isoleucine with vigorous stirring to ensure good dispersion. Measure the pH and add citric acid as necessary to bring the pH into the range 4.5–5.0.

Method 2:

Form a shear gel using the method described for the shampoo composition in Example 1. Separately, prepare a concentrated conditioner by heating together a small amount of water, cetrimonium chloride and cetearyl alchohol. Cool with stirring until the temperature falls to 25 deg C. To the preformed shear gel add the concentrated conditioner, polydimethylsiloxane emulsion, perfume, methyl paraben, D-glucose and L-isoleucine with vigorous stirring to ensure good dispersion. Measure the pH and add citric acid as necessary to bring the pH into the range 4.5–5.0.

What is claimed is:

1. A hair treatment composition which is a shampoo and has a thickened fluid form comprising:
    (i) a first phase comprising at least one naturally derived polymer which is capable of forming a reversible gel, which copolymer is present in the composition as a shear gel having a multiplicity of separate gel particles which have been formed by subjecting the polymer to shear while gel formation takes place, and
    (ii) a second phase suspended therein,
    said composition further comprising:
    (a) from 5 to 30% by weight of the total shampoo composition of surfactant, and
    (b) from 0.02% to 0.5% by weight of the total shampoo composition of a cationic deposition polymer.

2. A hair treatment composition which is a conditioner and has a thickened fluid form comprising:
    (i) a first phase comprising at least one naturally derived polymer which is capable of forming a reversible gel, which copolymer is present in the composition as a shear gel having a multiplicity of separate gel particles which have been formed by subjecting the polymer to shear while gel formation takes place, and
    (ii) a second phase suspended therein,
    said composition further comprising:
    (a) from 0.05 to 5% by weight of the total composition of a cationic surfactant, and
    (b) from 0.1 to 5% by weight of the total composition of a fatty alcohol.

* * * * *